United States Patent
Acland et al.

(10) Patent No.: US 8,147,823 B2
(45) Date of Patent: Apr. 3, 2012

(54) METHOD OF TREATING OR RETARDING THE DEVELOPMENT OF BLINDNESS

(75) Inventors: Gregory M. Acland, Kennett Square, PA (US); Gustavo D. Aguirre, Ithaca, NY (US); Jean Bennett, Bryn Mawr, PA (US); William W. Hauswirth, Gainesville, FL (US); Samuel G. Jacobson, Penn Valley, PA (US); Albert M. Maguire, Bryn Mawr, PA (US)

(73) Assignees: The Trustees of the University of Pennsylvania, Philadelphia, PA (US); University of Florida Research Foundation, Incorporated, Gaineville, FL (US); Cornell Research Foundation Inc., Ithaca, NY (US)

( * ) Notice: Subject to any disclaimer, the term of this patent is extended or adjusted under 35 U.S.C. 154(b) by 0 days.

(21) Appl. No.: 12/832,282

(22) Filed: Jul. 8, 2010
(Under 37 CFR 1.47)

(65) Prior Publication Data
US 2010/0272688 A1  Oct. 28, 2010

Related U.S. Application Data

(63) Continuation of application No. 12/253,955, filed on Oct. 18, 2008, now abandoned, which is a continuation of application No. 11/511,201, filed on Aug. 28, 2006, now abandoned, which is a continuation of application No. 10/300,720, filed on Nov. 20, 2002, now abandoned, which is a continuation of application No. PCT/US02/11314, filed on Apr. 11, 2002.

(60) Provisional application No. 60/283,766, filed on Apr. 13, 2001.

(51) Int. Cl.
*A61K 48/00* (2006.01)
*C12N 15/12* (2006.01)
*C12N 15/861* (2006.01)

(52) U.S. Cl. ......... 424/93.6; 424/93.2; 435/456; 514/44

(58) Field of Classification Search ................ 424/93.2, 424/93.6; 435/456; 524/44
See application file for complete search history.

(56) References Cited

U.S. PATENT DOCUMENTS

| | | | |
|---|---|---|---|
| 5,789,390 A | 8/1998 | Descamps et al. | |
| 5,827,702 A | 10/1998 | Cuthbertson | |
| 6,201,114 B1 | 3/2001 | Aguirre et al. | |
| 6,204,251 B1 | 3/2001 | Cuthbertson | |
| 6,261,551 B1 | 7/2001 | Wilson et al. | |
| 6,759,237 B1 | 7/2004 | Wilson et al. | |
| 6,770,663 B2 | 8/2004 | Wagle et al. | |
| 6,943,153 B1 | 9/2005 | Manning et al. | |
| 7,090,864 B2 | 8/2006 | Pardridge | |
| 2002/0054902 A1 | 5/2002 | Partridge | |
| 2002/0193327 A1 | 12/2002 | Nemerow et al. | |
| 2002/0194630 A1 | 12/2002 | Manning et al. | |
| 2003/0165486 A1* | 9/2003 | Karageozian | 424/94.61 |
| 2005/0255089 A1 | 11/2005 | Chiorini et al. | |
| 2007/0077228 A1 | 4/2007 | Acland et al. | |

FOREIGN PATENT DOCUMENTS

| | | |
|---|---|---|
| WO | WO-98/48027 | 10/1998 |
| WO | WO-00/15822 | 3/2000 |
| WO | WO 2009/134681 A2 | 11/2009 |

OTHER PUBLICATIONS

Yakely, J. Am. Vet. Med. Assoc. 161(10):1103-1107, 1972; Citation only.*
Sampson, Veterinary J. 189:136-140, 2011.*
Okabe et al, FEBS Lett. 407(3):313-319, 1997; Abstract only.*
Jomary et al, Gene Therapy 4:683-690, 1997.*
Das et al, Experimental Neurology 157: 58-68, 1999.*
Humayun et al, Invest. Opthalmol. Vis. Sci. 41:3100-3106, 2000.*
Pederson et al, Arch. Opthalmol. 100(7):1150-1154, 1982.*
Acland, et al., Gene Therapy Restores Vision in a Canine Model of Childhood Blindness, Nature Genetics, May 2001, pp. 92-95, vol. 28.
Coco, et al., Pharmacokinetics of Intravitreal Vancomycin in Normal and Infected Rabbit Eyes, Journal of Ocular Pharmacology and Therapeutics, 1998, pp. 555-562, vol. 14, No. 6.
Cook, et al., Apoptotic Photoreceptor Degeneration in Experimental Retinal Detachment, Investigative Opthalmology & Visual Science, May 1995, pp. 990-996, vol. 36, No. 6.
Dudus, et al., Persistent Transgene Product in Retina, Optic Nerve and Brain After Intraocular Injection of rAAV, Vision Research, 1999, pp. 2545-2553, vol. 39.
Imai, et al., Translocation of the Retina for Management of Subfoveal Choroidal Neovascularization I: Experimental Studies in the Rabbit Eye, Am. J. Opthalmol., 1998, pp. 627-634, vol. 125.
Juan, et al., Translocation of the Retina for Management of Subfoveal Choroidal Neovascularization II: A Preliminary Report in Humans, Am. J. Opthalmol., 1998, pp. 635-646, vol. 25.

(Continued)

*Primary Examiner* — Kevin K. Hill
(74) *Attorney, Agent, or Firm* — Howson & Howson LLP

(57) ABSTRACT

A method for treating an ocular disorder characterized by the defect or absence of a normal gene in the ocular cells of a human or animal subject involves administering to the subject by subretinal injection an effective amount of a recombinant adeno-associated virus carrying a nucleic acid sequence encoding the normal gene under the control of a promoter sequence which expresses the product of the gene in the ocular cells. The ocular cells are preferably retinal pigment epithelial (RPE) cells, and the gene is preferably an RPE-specific gene, e.g., RPE65. The promoter is one that can express the gene product in the RPE cells. Compositions for subretinal administration are useful in this method.

8 Claims, No Drawings

OTHER PUBLICATIONS

Lewis, et al., Animal Models of Retinal Detachment and Reattachment: Identifying Cellular Events That May Affect Visual Recovery, Eye, 2002, pp. 375-387, vol. 16.
Maguire, et al., Age-Dependent Effects of RPE65 Gene Therapy for Leber's Congenital Amaurosis: A Phase 1 Dose-Escalation Trial, The Lancet, Oct. 24, 2009, pp. 1-25, DOI:10.1016/S0140-6736(09)61836-5.
Reichel, et al., Gene Transfer in Opthalmology, Opthalmologe, 1999, pp. 570-577, vol. 96.
Ray, et al., Adeno-Associated Virus Mediated Gene Transfer in the Retinal Pigment Epithelium of the RPE65 Mutant Dog, JOVS, Mar. 15, 2001, vol. 42, No. 4 (Abstract).
Ryan (Editor), Retina Third Edition, 2001, pp. 2580-2596, Chapter 155.
Verdugo, et al., Posterior Segment Approach for Subretinal Transplantation or Injection in the Canine Model, Cell Transplantation, 2001, pp. 317-327, vol. 10.
Office Action dated Jul. 15, 2009 in parent U.S. Appl. No. 12/253,955.
Response to Office Action dated Jul. 15, 2009 in parent U.S. Appl. No. 12/253,955.
Declaration under 37 CFR 1.131 (re: *Ray* 2001) accompanying Response to Office Action dated Jul. 15, 2009 in parent U.S. Appl. No. 12/253,955.
Declaration under 37 CFR 1.132 accompanying Response to Office Action dated Jul. 15, 2009 in parent U.S. Appl. No. 12/253,955.
Office Action dated Mar. 9, 2010 in parent U.S. Appl. No. 12/253,955.
Pre-Appeal Brief Request for Review in parent U.S. Appl. No. 12/253,955.
Notice of Panel Decision from Pre-Appeal Brief Review in parent U.S. Appl. No. 12/253,955.
Acland et al., Long-Term Restoration of Rod and Cone Vision by Single Dose rAAV-Mediated Gene Transfer to the Retina in a Canine Model of Childhood Blindness, Molecular Therapy, 12(6)1072-1082 (Dec. 2005 Epub: Oct. 14, 2005).
Aleman et al., "Impairment of the Transient Pupillary Light Reflex in Rpe65(-/-) Mice and Humans With Leber Congenital Amaurosis", Invest Ophthalmol Vis Sci., 45(4):1259-1271 (Apr. 2004).
Ali at al., "Gene Transfer into the Mouse Retina Mediated by an Adeno-associated Viral Vector", Hum. Mol. Gen., 5(5):591-594 (May 1996).
Ali et al., "Restoration of Photoreceptor Ultrastructure and Function in Retinal Degeneration Slow Mice by Gene Therapy", Nat. Genet., 25:306-310 (Jul. 2000).
Anand et al., "A Deviant Immune Response to Viral Proteins and Transgene Product Is Generated on Subretinal Administration of Adenovirus and Adeno-Associated Virus", Molecular Therapy, 5(2)125-132 (Feb. 2002).
Auricchio et al., "Exchange of Surface Proteins Impacts on Viral Vector Cellular Specificity and Transduction Characteristics: The Retina as a Model", Hum. Mol. Gen., 10(26):3075-3081 (Dec. 15, 2001).
Bennett et al., "Gene Therapy for Ocular Disease", Mol. Ther., 1(6):501-505 (Jun. 2000).
Bennett et al., "Photoreceptor Cell Rescue in Retinal Degeneration (rd) Mice by In Vivo Gene Therapy", Nat. Med., 2(6): 649-654 (Jun. 6, 1996).
Bennett et al., "Stable Transgene Expression in Rod Photoreceptors After Recombinant Adeno-associated Virus-mediated Gene Transfer to Monkey Retina", Proc. Natl. Acad. Sci. USA, 96:9920-9925 (Aug. 1999).
Bennett et al., "Adenovirus-Mediated Delivery of Rhodopsin-Promoted bcl-2 Results in a Delay in Photoreceptor Cell Death in the rd/rd Mouse", Gene Ther., 5:1156-1164 (Sep. 1998).
Bennett, "Commentary: An Aye For Eye Gene Therapy", Hum Gene Ther., 17(2):177-179 (Feb. 2006).
Bennett, "Retinal Progenitor Cells—Timing Is Everything", N Engl J Med., 356(15):1577-1579 (Apr. 12, 2007).

Bennicelli et al., "Reversal of Blindness in Animal Models of Leber Congenital Amaurosis Using Optimized AAV2-Mediated Gene Transfer", Mol Ther., 16(3):458-465 (Mar. 2008 Epub Jan. 22, 2008).
Cremers et al., "Molecular Genetics of Leber Congenital Amaurosis", Hum. Mol. Genet., 11(10):1169-1176 (Mar. 2002).
D'Cruz et al., "Mutation of the Receptor Tyrosine Kinase Gene Mertk in the Retinal Dystrophic RCS Rat", Hum. Mol. Genet., 9(4):645-651 (Mar. 1, 2000).
Dejneka et al., In Utero Gene Therapy Rescues Vision in a Murine Model of Congenital Blindness, Mol. Ther., 9(2):182-188 (Feb. 2004).
Dryja et al., "A Point Mutation of the Rhodopsin Gene in One Form in Retinitis Pigmentosa", Nature, 343:364-366 (Jan. 25, 1990).
Farrar et al., "A Three-Base-Pair Deletion in the Peripherin-RDS Gene in One Form of Retinitis Plgmentosa", Lett. to Nature, 354:478-480 (Dec. 12, 1991).
Gian-Marco Sarra et al., "Gene Replacement Therapy in the Retinal Degeneration Slow (RS) Mouse: The Effect on Retinal Degeneration Following Partial Transduction of the Retina" Hum. Mol. Genetics, 10(21):2353-2361 (Oct. 1, 2001).
Gu et al., "Mutations in the RPE65 Cause Autosomal Recessive Childhood-Onset Severe Retinal Dystrophy", Nat. Genet., 17:194-197 (Oct. 1997).
Hauswirth, "Treatment of Leber Congenital Amaurosis Due to *RPE65* Mutations by Ocular Subretinal Injection of Adeno-Associated Virus Gene Vector: Short-Term Results of a Phase I Trial", Human Gene Therapy, 19:979-990 (Oct. 2008).
Jacobson et al., "Identifying Photoreceptors in Blind Eyes Caused by RPE65 Mutations: Prerequisite For Human Gene Therapy Success", Proc Natl Acad Sci U S A., 102(17):6177-6182 (Apr. 26, 2005 Epub: Apr. 18, 2005).
Jacobson et al., "Safety in Nonhuman Primates of Ocular AAV2-RPE65, A Candidate Treatment For Blindness in Leber Congenital Amaurosis", Hum Gene Ther., 17(8):845-858 (Aug. 2006).
Jacobson et al., "Safety of Recombinant Adeno-Associated Virus Type 2-RPE65 Vector Delivered by Ocular Subretinal Injection", Mol Ther., 13(6):1074-1084 (Jun. 2006 Epub: Apr. 27, 2006).
Kumar-Singh et al., "Encapsidated Adenovirus Mini-Chromosome-Mediated Delivery of Genes to the Retina: Application to the Rescue of Photoreceptor Degeneration", Hum. Mol. Genet., 7(12):1893-1900 (Nov. 1998).
Lau et al., "Retinal Degeneration is Slowed in Transgenic Rats by AAV-Mediated Delivery of FGF-2", Invest. Opthalmol. Vis. Sci., 41(11):3622-3633 (Oct. 2000).
Lavail et al., "Ribozyme Rescue of Photoreceptor Cells in P23H Transgenic Rats: Long-term Survival and Late-Stage Therapy", Proc. Natl. Acad. Sci. USA, 97:11488-11493 (Oct. 10, 2000).
Lebherz et al., "Novel AAV Serotypes For Improved Ocular Gene Transfer", J Gene Med., 10(4):375-382 (Apr. 2008).
Lewin et al., "Ribozyme Rescue of Photoreceptor Cells in a Transgenic Rat Model of Autosomal Dominant Retinitis Pigmentosa", Nat. Med., 4(8):967-971 (Aug. 1998).
Li et al., "Phenotype correction in retinal pigment epithelium in murine mucopolysaccharidosis VII by adenovirus-mediated gene transfer", Proc. Natl. Acad. Sci. USA, 92(17):7700-7704 (Aug. 15, 1995).
Maguire et al., "Safety and Efficacy of Gene Transfer for Leber's Congenital Amaurosis", N. Engl. J. Med., 358(21):2240-2248 (May 22, 2008 Epub: Apr. 27, 2008).
Marlhens et al., "Mutations in RPE65 Cause Leber's Congenital Amaurosls", Net Genet., 17:139-141 (Oct. 1997).
McLaughlin et al., "Recessive Mutations in the Gene Encoding the β-Subunit of Rod Phosphodiesterase in Patients with Retinitis Pigmentosa", Nat, Genet., 4:130-134 (Jun. 1993).
Mori et al., "AAV-Medieted Gene Transfer of Pigment Epithelium-Derived Factor Inhibits Choroidal Neovascularization", Invest. Opthalmol. and Vis. Sci., 43(6):1994-2000 (Jun. 2002).
Perrault et al., "Leber Congenital Amaurosis", Mol. Gen. Meta., 68(2):200-208 (Oct. 1999).
Petrukin et al., "Identification of the Gene Responsible for Best Macular Dystrophy", Nat. Genet., 19:241-247 (Jul. 1998).
Reich, "Gene Therapy For Ocular Neovascularization: A Cure in Sight", Curr Opin Genet Dev., 13(3):317-322 (Jun. 2003).

Rolling et al., "Long-term Real-time Monitoring of Adeno-associated Virus-Mediated Gene Expression in the Rat Retina", Clin. and Exp. Opthalmol., 28:382-386, (Oct. 2000).

Takahashi et al., "Rescue from Photoreceptor Degeneration in the rd Mouse by Human Immunodeficiency Virus Vector-Mediated Gene Transfer", J, Virol., 73:7812-7816. (Sep. 1999).

Zhang et al., "High-Titer Recombinant Adeno-Associated Virus Production from Replicating Amplicons and Herpes Vectors Deleted for Glycoprotein H", Hum. Gene Ther., 10:2527-2537. (Oct. 10, 1999).

Rosenberg, "Gene Therapist, Heal Thyself", 287(5459):1751 (Mar. 10, 2000).

Friedmann, "Medical Ethics. Principles For Human Gene Therapy Studies", Science. 287(5461):2163-2165 (Mar. 24, 2000).

Touchette, "Gene Therapy: Not Ready For Prime Time", Nature Medicine 2:7-8 (Jan. 1, 1996).

Borras, "Recent Developments in Ocular Gene Therapy", Exp Eye Res. 76(6):643-652 (Jun. 2003).

McGee Sanftner, "Glial Cell Line Derived Neurotrophic Factor Delays Photoreceptor Degeneration in a Transgenic Rat Model of Retinitis Pigmentosa", Mol Ther. 4(6):622-629 (Dec. 2001).

Office Action dated Sep. 20, 2005 in parent U.S. Appl. No. 10/300,720.

Response to Office Action dated Sep. 20, 2005 in parent U.S. Appl. No. 10/300,720.

Office Action dated May 30, 2006 in parent U.S. Appl. No. 10/300,720.

Office Action dated Aug. 15, 2007 in parent U.S. Appl. No. 11/511,201.

Response to Office Action dated Aug. 15, 2007 in parent U.S. Appl. No. 11/511,201.

Office Action dated Feb. 19, 2008 in parent U.S. Appl. No. 11/511,201.

Akimoto, et al., Adeno-virally Expressed Basic Fibroblast Growth Factor Rescues Photoreceptor Cells in RCS Rats, Investigative Ophthalmology & Visual Science, Feb. 1999, pp. 273-279, vol. 40.

Anand, et al., Additional Transduction Events After Subretinal Readministration of Recombinant Adeno-Associated Virus, Human Gene Therapy, Feb. 2000, pp. 449-457, vol. 11.

Bennett, et al., Real-time Non-invasive in Vivo Assessment of Adeno-associated Virus-mediated Retinal Transduction, Investigative Ophthalmology & Visual Science, Dec. 1997, pp. 2857-2863, vol. 38.

Cayouette, et al., Intraocular Gene Transfer of Ciliary Neurotrophic Factor Prevents Death and Increases Responsiveness of Rod Photoreceptors in the Retinal Degeneration Slow Mouse, The Journal of Neuroscience: The Official Journal of the Society for Neuroscience, Nov. 1998, pp. 9282-9293, vol. 18.

Cayouette, et al., Adenovirus-mediated Gene Transfer of Ciliary Neurotrophic Factor can Prevent Photoreceptor Degeneration in the Retinal Degeneration (rd) Mouse, Human Gene Therapy, Mar. 1997, pp. 423-430, vol. 8.

Chen, et al., Bcl-2 Overexpression Reduces Apoptotic Photoreceptor Cell Death in Three Different Retinal Degenerations, Proceedings of the National Academy of Sciences of the United States of America, Jul. 1996, pp. 7042-7047, vol. 93.

Flannery, et al., Transgenic Animal Models for the Study of Inherited Retinal Dystrophies, Institute for Laboratory Animal Research Journal, 1999, pp. 55-58, vol. 40 (2).

Flannery, et al., Efficient Photoreceptor-targeted Gene Expression in Vivo by Recombinant Adeno-Associated Virus, Proceedings of the National Academy of Sciences of the United States of America, Jun. 1997, pp. 6916-6921, vol. 94.

Green, et al., Two Animal Models of Retinal Degeneration are Rescued by Recombinant Adeno-Assocaited Virus-Mediated Production of GFG-5 and GFG-18, Molecular Therapy, Apr. 2001, pp. 507-515, vol. 3.

Green, et al., Characterization of Rhodopsin Mis-sorting and Constitutive Activation in a Transgenic Rat Model of Autosomal Dominant Retinitis Pigmentosa, Investigative Ophthalmology & Visual Science, May 2000, pp. 1546-1553, vol. 41.

Jomary, et al., Rescue of Photoreceptor Function by AAV-Mediated Gene Transfer in a Mouse Model of Inherited Retinal Degeneration, Gene Therapy, Jul. 1997, pp. 683-690, vol. 4.

Lem, et al., Retinal Degeneration is Rescued in Transgenic RD Mice by Expression of the CGMP Phosphodiesterase Beta Subunit, Proceedings of the National Academy of Sciences of the United States of America, May 1992, pp. 4422-4426, vol. 89.

Lem, et al., Tissue-specific and Developmental regulation of Rod Opsin Chimeric Genes in Transgenic Mice, Neuron, Feb. 1991, pp. 201-210, vol. 6.

McGee, et al., Glial Cell Line Derived Neurotrophic Factor Delays Photoreceptor Degeneration in a Transgenic Rat Model of Retinitis Pigmentosa, Molecular Therapy, Dec. 2001, pp. 622-629, vol. 4.

McGee, et al., Recombinant AAV-Mediated Delivery of a Tet-Inducible Reporter Gene to the Rat Retina, Molecular Therapy, May 2001, pp. 688-696, vol. 3.

Ogneta, et al., The Human CHMP-PDE Beta-Subunit Promoter Region Directs Expression of the Gene to Mouse Photoreceptors, Investigative Ophthalmology & Visual Science, Dec. 2000, pp. 4059-4063, vol. 41.

Videos contained on the webpage located at http://www.uphs.upenn.edu/news/News_Releases/2009/10/gene-therapy-restores-sight/videos.html (printed version of the webpage enclosed).

* cited by examiner

METHOD OF TREATING OR RETARDING THE DEVELOPMENT OF BLINDNESS

CROSS-REFERENCE TO RELATED APPLICATIONS

This application is a continuation of U.S. patent application Ser. No. 12/253,955, filed Oct. 18, 2008, which is a continuation of U.S. patent application Ser. No. 11/511,201, filed Aug. 28, 2006, now abandoned, which is a continuation of U.S. patent application Ser. No. 10/300,720, filed Nov. 20, 2002, now abandoned, which is a continuation of International Patent Application No. PCT/US02/11314, filed Apr. 11, 2002, which claims the benefit of the priority of U.S. Provisional Patent Application No. 60/283,766, filed Apr. 13, 2001, now abandoned, which applications are incorporated by reference.

STATEMENT REGARDING FEDERALLY SPONSORED RESEARCH OR DEVELOPMENT

This invention was made with government support under Grant Nos. EY010820, EY011123, EY006855, NS036202, EY011142, and EY013132 awarded by the National Institutes of Health. The government has certain rights in this invention.

BACKGROUND OF THE INVENTION

The invention relates generally to the use of recombinant viruses to deliver a desired transgene to retinal pigment epithelial cells of patients suffering from retinal degenerative diseases.

The relationship between the neurosensory photoreceptors and the adjacent retinal pigment epithelium (RPE) controls not only normal retinal function, but also the pathogenesis of hereditary retinal degenerations. Recent progress has identified the molecular bases for primary photoreceptor diseases, such as retinitis pigmentosa (Dryja, T. P., et al. 1990 *Nature* 343, 364-366; Farrar, G. J., et al. 1991 *Nature* 354, 478-480; and McLaughlin, M. E. et al, 1993 *Nature Genetics* 4, 130-134). Similarly the molecular bases for RPE diseases that cause photoreceptor blindness, such as child-onset severe retinal dystrophy, Leber's congenital amaurosis, and Best macular dystrophy, have been identified (Gu, S.-M., et al. 1997 *Nature Genetics* 17, 194-197; Marlhens, F., et al. 1997 *Nature Genetics* 17, 139-141; Petrukin, K., et al. 1998 *Nature Genet* 19, 241-247; and D'Cruz, P., et al. 2000 *Hum. Mol. Genet.* 9, 645-651). Despite these reported scientific advances, effective therapy for human retinal degenerations is still lacking.

Retinal gene therapy has been considered a possible therapeutic option for man. For example, U.S. Pat. No. 5,827,702 refers to methods for generating a genetically engineered ocular cell by contacting the cell with an exogenous nucleic acid under conditions in which the exogenous nucleic acid is taken up by the cell for expression. The exogenous nucleic acid is described as a retrovirus, an adenovirus, an adeno-associated virus or a plasmid. See, also, International Patent Publication Nos. WO 00/15822, published Mar. 23, 2000 and WO 98/48097, published Oct. 29, 1998.

A review of gene therapy efforts to date indicates that such efforts have focused mainly on slowing down retinal degeneration in rodent models of primary photoreceptor diseases. Normal genes and mutation-specific ribozymes delivered to photoreceptors have prolonged the lifetime of these cells otherwise doomed for apoptotic cell death (Bennett, J., et al. 1996 *Nat. Med.* 2, 649-654; Bennett, J., et al. 1998 *Gene Therapy* 5, 1156-1164; Kumar-Singh, R. & Farber, D., 1998 *Hum. Mol. Genet.* 7, 1893-900; Lewin, A. S., et al. 1998 *Nat. Med.* 4, 967-971; Ali, R., et al. 2000 *Nat. Genet.* 25, 306-310; Takahashi, M. et al, 1999 *J. Virol.* 73, 7812-6; Lau, D., et al. 2000 *Invest. Ophthalmol. Vis. Sci.* 41, 3622-3633; and LaVail, M. M., et al. 2000 *Proc Natl Acad Sci USA* 97, 11488-11493).

Retinal gene transfer of a reporter gene, green fluorescent protein, using a recombinant adeno-associated virus was demonstrated in normal primates (Bennett, J., et al. 1999 *Proc. Natl. Acad. Sci. USA* 96, 9920-9925). However, an as-yet unmet goal of research is the restoration of vision in a blinding disease of animals, particularly humans and other mammals, caused by genetic defects in RPE and/or photoreceptor cells.

There remains a need in the art for methods for effectively treating humans and other mammals or other animals suffering from blindness due to genetic defects or deficiencies, so as to restore sufficient vision to enable the subject to function in response to visual cues.

SUMMARY OF THE INVENTION

In one aspect, the invention provides a method for treating an ocular disorder in a human or animal subject characterized by the defect or absence of a normal gene in the ocular cells. The method includes administering to the subject by subretinal injection an effective amount of a recombinant adeno-associated virus carrying a nucleic acid sequence encoding the normal gene under the control of a promoter sequence which expresses the product of the gene in the ocular cells.

In another aspect, the invention provides a method for treating an ocular disorder in a human or animal subject characterized by the defect or absence of a normal gene in the retinal pigment epithelial (RPE) cells of the subject. The method involves administering to the subject by subretinal injection an effective amount of a recombinant virus carrying a nucleic acid sequence encoding a normal retinal pigment epithelial (RPE) cell-specific gene under the control of a promoter sequence which expresses the product of the gene in RPE cells. In one embodiment, the gene is the RPE65 gene.

In another aspect, the invention provides a method for treating Leber congenital amaurosis in a subject by administering to the subject by subretinal injection an effective amount of a recombinant virus carrying a nucleic acid sequence encoding a normal gene under the control of a promoter sequence which expresses the product of the gene in ocular cells, wherein the cells contain a mutated version of the gene. Expression of the normal gene provides to the cells the product necessary to restore or maintain vision in the subject. In one embodiment, the cells are RPE or photoreceptor cells, and the promoters are cell-specific promoters.

In still another embodiment, the invention provides a composition for treatment of an ocular disorder characterized by the defect or absence of a normal gene in the ocular cells of the subject. Such compositions comprise effective amounts of a recombinant adeno-associated virus carrying a nucleic acid sequence encoding the normal gene under the control of a promoter sequence which expresses the product of the gene in the ocular cells, formulated with a carrier and additional components suitable for subretinal injection. In one embodiment, the normal gene is RPE65.

Other aspects and advantages of the present invention are described further in the following detailed description of the preferred embodiments thereof.

DETAILED DESCRIPTION OF THE INVENTION

The invention provides a method for treating an ocular disorder in a human, other mammalian or other animal subject. In particular, the ocular disorder is one which involves a mutated or absent gene in a retinal pigment epithelial cell or a photoreceptor cell. The method of this invention comprises the step of administering to the subject by subretinal injection an effective amount of a recombinant virus carrying a nucleic acid sequence encoding an ocular cell-specific normal gene operably linked to, or under the control of, a promoter sequence which directs the expression of the product of the gene in the ocular cells and replaces the lack of expression or incorrect expression of the mutated or absent gene.

A. The Ocular Disorder

In particular, this method is useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by this method. Thus, the particular ocular disorder treated by this method may include the above-mentioned disorders and a number of diseases which have yet to be so characterized. For purposes of illustration of this invention, the particular ocular disorder being treated in the examples is Leber congenital amaurosis, which affects humans. However, this invention is not limited to the treatment of that disorder alone.

Leber congenital amaurosis (LCA) is a severe childhood-onset blinding disease which can be caused by mutations in the retinal pigment epithelium (RPE)-specific gene, RPE65. A naturally-occurring large animal model of an analogous severe disease of retinal degenerations is the RPE65 mutant dog. LCA causes near total blindness from early in life. Among the molecular causes of LCA are mutations in the gene encoding an RPE protein, RPE65. RPE65 is an evolutionarily-conserved 65 kDa membrane-associated protein (Redmond, T. & Hamel, C. 2000 *Meth. Enzymol.* 317, 705-724 and Bavik, C. et al, 1992 *J. Biol. Chem.* 267, 23035-23042), which is important in retinoid metabolism (Saari, J. 2000 *Invest Ophthalmol Vis Sci* 41, 337-348; Ma, J.-X. et al, 1998 *J Biol Chem* 1443, 255-261; and Simon, A. et al, 1995 *J Biol Chem* 270, 1107-1112). Currently there is no treatment for LCA and related early onset retinal degenerative diseases.

RPE65 deficiency in mice results in accumulation of all-trans-retinyl esters, undetectable levels of rhodopsin, rod photoreceptor dysfunction, inclusions in the RPE, and slow retinal degeneration. The compound 9-cis-retinal can restore visual pigment and function in RPE65-deficient mice (Redmond, T., et al. 1998 *Nat. Genet* 20, 344-351 and Van Hooser, J. P., et al. 2000 *Proc. Natl Acad Sci USA* 97, 8623-8628).

The RPE65 mutant dog shows early and severe visual impairment caused by a homozygous 4 bp-deletion in the RPE65 gene. The deletion results in a frame shift leading to a premature stop codon, eliminating more than two-thirds of the wildtype polypeptide. Histopathology in homozygotes shows prominent RPE inclusions and slightly abnormal rod photoreceptor morphology present within the first year of life, and slowly progressive photoreceptor degeneration in older dogs. See, e.g., Wrigstad, A. Hereditary Dystrophy of the Retina and the Retinal Pigment Epithelium in a Strain of Briard Dogs: A Clinical, Morphological and Electrophysiological Study. *Linkoping University Medical Dissertations* (1994); Narfstrom, K. et al, 1989 *Brit J Ophthalmol.* 73, 750-756; and Aguirre, G., et al. 1998 *Mol. Vis.* 4, 23.

B. Vectors for Use in the Method

According to the various embodiments of the present invention, a variety of known nucleic acid vectors may be used in these methods, e.g., recombinant viruses, such as recombinant adeno-associated virus (AAV), recombinant adenoviruses, recombinant retroviruses, recombinant poxviruses, and other known viruses in the art, as well as plasmids, cosmids and phages, etc. A wealth of publications known to those of skill in the art discusses the use of a variety of such vectors for delivery of genes (see, e.g., Ausubel et al., *Current Protocols in Molecular Biology*, John Wiley & Sons, New York, 1989; Kay, M. A. et al, 2001 *Nat. Medic.*, 7(1):33-40; and Walther W. and Stein U., 2000 *Drugs*, 60(2):249-71). In one embodiment of this invention the vector is a recombinant AAV carrying a wildtype (i.e., normal) version of a selected transgene-encoding cDNA driven by a promoter that expresses the product of the wildtype cDNA in selected ocular cells of the affected subject. Methods for assembly of the recombinant vectors are well-known (see, e.g., International Patent Publication No. WO 00/15822, published Mar. 23, 2000 and other references cited herein). To exemplify the methods and compositions of this invention, the presently preferred vector, a recombinant AAV is described in detail.

1. AAV Vectors

Adeno-associated viruses are small, single-stranded DNA viruses which require helper virus to facilitate efficient replication (K. I. Berns, *Parvoviridae: the viruses and their replication*, p. 1007-1041, in F. N. Fields et al., Fundamental Virology, 3rd ed., vol. 2, (Lippencott-Raven Publishers, Philadelphia, Pa.) (1995)). The 4.7 kb genome of AAV is characterized by two inverted terminal repeats (ITR) and two open reading frames which encode the Rep proteins and Cap proteins, respectively. The Rep reading frame encodes four proteins of molecular weight 78 kD, 68 kD, 52 kD and 40 kD. These proteins function mainly in regulating AAV replication and rescue and integration of the AAV into a host cell's chromosomes. The Cap reading frame encodes three structural proteins of molecular weight 85 kD (VP1), 72 kD (VP2) and 61 kD (VP3) (Berns, cited above) which form the virion capsid. More than 80% of total proteins in AAV virion comprise VP3.

Flanking the rep and cap open reading frames at the 5' and 3' ends are 145 by inverted terminal repeats (ITRs), the first 125 by of which are capable of forming Y- or T-shaped duplex structures. The two ITRs are the only cis elements essential for AAV replication, rescue, packaging and integration of the AAV genome. There are two conformations of AAV ITRs called "flip" and "flop". These differences in conformation originated from the replication model of adeno-associated virus which uses the ITR to initiate and reinitiate the replication (R. O. Snyder et al, 1993, *J. Virol.*, 67:6096-6104 (1993); K. I. Berns, 1990 *Microbiological Reviews*, 54:316-329). The entire rep and cap domains can be excised and replaced with a therapeutic or reporter transgene (B. J. Carter, in "Handbook of Parvoviruses", ed., P. Tijsser, CRC Press, pp. 155-168 (1990)).

AAVs have been found in many animal species, including primates, canine, fowl and human (F. A. Murphy et al., "The Classification and Nomenclature of Viruses: Sixth Report of the International Committee on Taxonomy of Viruses", Archives of Virology, (Springer-Verlag, Vienna) (1995)). Six primate serotypes have been reported (AAV1, AAV2, AAV3, AAV4, AAV5 and AAV6). The AAV ITR sequences and other AAV sequences employed in generating the minigenes, vectors, and capsids, and other constructs used in the present invention may be obtained from a variety of sources. For example, the sequences may be provided by AAV type 5, AAV type 2, AAV type 1, AAV type 3, AAV type 4, AAV type 6, or other AAV serotypes or other adenoviruses, including presently identified human AAV types and AAV serotypes yet to be identified. Similarly, AAVs known to infect other animals may also provide these ITRs employed in the molecules or constructs of this invention. Similarly, the capsids from a variety of serotypes of AAV may be "mixed and matched" with the other vector components. See, e.g., International Patent Publication No. WO 01/83692, published Nov. 8, 2001, and incorporated herein by reference. A variety of these viral serotypes and strains are available from the American Type Culture Collection, Manassas, Va., or are available from a variety of academic or commercial sources. Alternatively, it may be desirable to synthesize sequences used in preparing the vectors and viruses of the invention using known techniques, which may utilize AAV sequences which are published and/or available from a variety of databases. The source of the sequences utilized in preparation of the constructs of the invention, is not a limitation of the present invention. Similarly, the selection of the species and serotype of AAV that provides these sequences is within the skill of the artisan and does not limit the following invention.

2. The Minigene

For use in the present invention, the AAV sequences are typically in the form of a rAAV construct (e.g., a minigene or cassette) which is packaged into a rAAV virion. At a minimum, the rAAV minigene useful in this invention is formed by AAV inverted terminal repeat sequences (ITRs) and a heterologous molecule for delivery to a host cell. Most suitably, the minigene contains AAV 5' ITRs and 3' ITRs located 5' and 3' to the heterologous molecule, respectively. However, in certain embodiments, it may be desirable for the minigene to contain the 5' ITR and 3' ITR sequences arranged in tandem, e.g., 5' to 3' or a head-to-tail, or in another alternative configuration. In still other embodiments, it may be desirable for the minigene to contain multiple copies of the ITRs or to have 5' ITRs (or conversely, 3' ITRs) located both 5' and 3' to the heterologous molecule. The ITRs sequences may be located immediately upstream and/or downstream of the heterologous molecule, or there may be intervening sequences. The ITRs may be selected from AAV5, or from among the other AAV serotypes, as described herein. Optionally, a minigene may contain 5' ITRs from one serotype and 3' ITRs from a second serotype. The AAV sequences employed are preferably the 145 by cis-acting 5' and 3' inverted terminal repeat sequences (See, e.g., B. J. Carter, cited above). Preferably, the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); Carter et al, cited above; and K. Fisher et al., 1996 *J. Virol.*, 70:520-532). One of skill in the art can readily engineer the rAAV virus by methods known to the art (e.g., Bennett, J., et al. 1999 *Proc. Natl. Acad. Sci. USA* 96, 9920-9925). An example of such a molecule employed in the present invention is a "cis-acting" plasmid containing the heterologous molecule flanked by the 5' and 3' AAV ITR sequences.

The heterologous molecule may be any substance which is desired to be delivered to a cell, including, without limitation, a polypeptide, protein, enzyme, carbohydrate, chemical moiety, or nucleic acid sequences which may include oligonucleotides, RNA, and/or DNA. Preferably, for use in this invention, the heterologous molecule is a selected transgene under the control of a selected promoter and other conventional vector regulatory components. See, e.g., U.S. Pat. Nos. 5,856, 152 and 5,871,982. In one embodiment, the heterologous molecule may be a nucleic acid molecule which introduces specific genetic modifications into human chromosomes, e.g., for correction of mutated genes. See, e.g., D. W. Russell & R. K. Hirata, 1998 *Nat. Genet.*, 18:325-330.

a. The Transgene

In another desirable embodiment, the heterologous molecule is a nucleic acid molecule is a transgene. As used herein, "transgene" refers to a nucleic acid sequence heterologous to the AAV sequence, encoding a desired product, e.g., a polypeptide or protein of interest, and the regulatory sequences which direct transcription and/or translation thereof in a host cell, and permit expression of the encoded product in a host cell. Suitable encoded products and regulatory sequences are discussed in more detail below. However, the selection of the heterologous molecule delivered by the AAV minigene is not a limitation of the present invention.

In one embodiment of the method, where the ocular disorder is caused by a mutation in a normal retinal pigment epithelium (RPE)-specific gene, the ocular cells which are the target of the treatment method are the retinal pigment epithelial (RPE) cells. The specific gene which is mutated or absent in the disorder may be the RPE65 gene. Another gene which is mutated or absent in the disorder in humans may be the arylhydrocarbon-interacting receptor protein like 1 (AIPL1). Thus, the normal gene, i.e., the transgene, present in the recombinant virus is the normal, species-matched version of the mutated gene, e.g., wildtype canine RPE65 for the treatment of canine LCA or wildtype human RPE65 for the treatment of human LCA, wildtype human AIPL1 for the treatment of a certain type of human blinding diseases, etc. In still another embodiment, the gene can be the CRB1 (RP12) gene. In another embodiment, the transgene can be the lecithin retinal acetyltransferase (LRAT) gene. These transgenes, as well as other transgenes useful for delivery to the eye may be obtained from conventional sources, e.g., from university laboratories or depositories, or synthesized from information obtained from Genbank by known techniques.

In another embodiment of the method, where the ocular disorder is caused by a mutation in a normal photoreceptor-specific gene, the ocular cells which are the target of the treatment method are the photoreceptor cells. The specific gene which is mutated or absent in the disorder may be the photoreceptor-specific homeo box gene (CRX). Alternatively, the specific gene which is mutated or absent in the disorder may be the retinal guanylate cyclase gene (GUCY2D). In still another embodiment, the transgene is a nucleotide sequence encoding RPGR Interacting Protein 1 (RPGRIP1). Thus, the normal gene, i.e., the transgene, present in the recombinant adeno-associated virus is the normal, species-matched version of the mutated gene, e.g., wildtype murine CRX for the treatment of the correlative murine blinding disorder or wildtype human CRX for the treatment of the correlative human blinding disorder, wildtype chicken GUCY2D for the treatment of the correlative chicken blinding disorder or wildtype human GUCY2D for the treatment of the correlative human blinding disorder, etc. These transgenes may be obtained from conventional sources, e.g., from university laboratories or depositories, or synthesized from information obtained from Genbank by known techniques.

As discussed above, still other genes may be added to this list, including the LCA genes referred to as LCA3, located at chromosome 14q24 and LCA5, located at chromosome 6q11-q16, among others.

Genes responsible for disorders other than LCA may also be employed as the transgene, as suitable ocular diseases are identified. Thus, different transgene may be used in the design of similar vectors of this invention for the treatment of disorders other than LCA. Among the known genes which may be absent or mutated in the blinding disorders identified above include dystrophin, ABCR, EMP1, TIMP3, MERTCK and ELOVL4. One or more of the wildtypes of these genes may be administered to ocular cells, particularly the RPE, in the same manner as is the exemplified RPE65 for the treatment of LCA. One of skill in the art may obtain the appropriate gene sequences and design the appropriate vectors for such use in view of this disclosure and in view of other information known to the art.

In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. In another embodiment, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., total of the DNA encoding the subunits and the IRES is less than five kilobases. Alternatively, other methods which do not require the use of an IRES may be used for co-expression of proteins. Such other methods may involve the use of a second internal promoter, an alternative splice signal, a co- or post-translational proteolytic cleavage strategy, among others which are known to those of skill in the art.

b. Regulatory Sequences

The minigene or transgene includes appropriate sequences that are operably linked to the nucleic acid sequences encoding the product of interest to promote its expression in a host cell. "Operably linked" sequences present in the minigene include both expression control sequences (e.g. promoters) that are contiguous with the coding sequences for the product of interest and expression control sequences that act in trans or at a distance to control the expression of the product of interest. In addition to being useful in the transgene, the regulatory elements described herein may also be used in other heterologous molecules and the other constructs described in this application.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein processing and/or secretion. A great number of expression control sequences, e.g., native, constitutive, inducible and/or tissue-specific, are known in the art and may be utilized to drive expression of the gene, depending upon the type of expression desired.

For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' ITR sequence. In one embodiment, the bovine growth hormone polyA is used.

The regulatory sequences useful in the constructs of the present invention may also contain an intron, desirably located between the promoter/enhancer sequence and the gene. One possible intron sequence is also derived from SV-40, and is referred to as the SV-40 T intron sequence. Another suitable sequence includes the woodchuck hepatitis virus post-transcriptional element. (See, e.g., L. Wang and I. Verma, 1999 *Proc. Nail. Acad. Sci., USA*, 96:3906-3910).

Another regulatory component of the rAAV useful in the method of the invention is an internal ribosome entry site (IRES). An IRES sequence, or other suitable systems as are discussed above, may be used to produce more than one polypeptide from a single gene transcript. An IRES (or other suitable sequence) is used to produce a protein that contains more than one polypeptide chain or to express two different proteins from or within the same cell. An exemplary IRES is the poliovirus internal ribosome entry sequence, which supports transgene expression in photoreceptors, RPE and ganglion cells. Preferably, the IRES is located 3=to the transgene in the rAAV vector.

The selection of the promoter to be employed in the rAAV may be made from among a wide number of constitutive or inducible promoters that can express the selected transgene in an ocular. In a preferred embodiment, the promoter is cell-specific. The term "cell-specific" means that the particular promoter selected for the recombinant vector can direct expression of the selected transgene is a particular ocular cell type. As one example, the promoter is specific for expression of the transgene in RPE cells. As another example, the promoter is specific for expression of the transgene in photoreceptor cells.

Examples of constitutive promoters which may be included in the rAAV of this invention include, without limitation, the exemplified CMV immediate early enhancer/chicken β-actin (CβA) promoter-exon 1-intron 1 element of Example 1, the RSV LTR promoter/enhancer, the SV40 promoter, the CMV promoter, the dihydrofolate reductase promoter, and the phosphoglycerol kinase (PGK) promoter.

RPE-specific promoters include, for example, the RPE-65 promoter, the tissue inhibitor of metalloproteinase 3 (Timp3) promoter, and the tyrosinase promoter. Still other RPE-specific promoters are known to those of skill in the art. See, e.g., the promoters described in International Patent Publication No. WO 00/15822.

Examples of photoreceptor specific promoters include, without limitation, the rod opsin promoter, the red-green opsin promoter, the blue opsin promoter, the inter photoreceptor binding protein (IRBP) promoter and the cGMP-β-phosphodiesterase promoter. See, e.g., the promoters described in International Patent Publication No. WO 98/48097.

Alternatively, an inducible promoter is employed to express the transgene product, so as to control the amount and timing of the ocular cell=s production thereof. Such promoters can be useful if the gene product proves to be toxic to the cell upon excessive accumulation. Inducible promoters include those known in the art and those discussed above including, without limitation, the zinc-inducible sheep metallothionine (MT) promoter; the dexamethasone (Dex)-inducible mouse mammary tumor virus (MMTV) promoter; the T7 promoter; the ecdysone insect promoter; the tetracycline-repressible system; the tetracycline-inducible system; the RU486-inducible system; and the rapamycin-inducible system. Any type of inducible promoter which is tightly regulated and is specific for the particular target ocular cell type may be used. Other types of inducible promoters which may be useful in this context are those which are regulated by a specific physiological state, e.g., temperature, acute phase, a particularly differentiation state of the cell, or in replicating cells only.

Selection of these and other common vector and regulatory elements are conventional and many such sequences are available. See, e.g., Sambrook et al, and references cited therein at, for example, pages 3.18-3.26 and 16.17-16.27 and Ausubel et al., *Current Protocols in Molecular Biology*, John Wiley & Sons, New York, 1989). Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct. For instance, one may select one or more expression control sequences, operably link the sequence to a transgene of interest, and insert the "minigene" comprising the expression control sequence and the transgene into an AAV vector. The vector may be packaged into an infectious particle or virion following one of the methods for packaging the rAAV taught in the art.

C. Production of the rAAV

The rAAV virus of the invention may be constructed and produced using the materials and methods described herein, as well as those known to those of skill in the art. Such engineering methods used to construct any embodiment of this invention are known to those with skill in nucleic acid manipulation and include genetic engineering, recombinant engineering, and synthetic techniques. See, e.g., Sambrook et al, and Ausubel et al., cited above; and International Patent Publication No. WO 95/13598. Further, methods suitable for producing a rAAV cassette in an adenoviral capsid have been described in U.S. Pat. Nos. 5,856,152 and 5,871,982.

Briefly, in order to package the rAAV construct into a rAAV virion, a host cell must contain sequences necessary to express AAV rep and AAV cap or functional fragments thereof as well as helper genes essential for AAV production. For example, the rep78/52 proteins may be sufficient to provide the necessary rep functions. The AAV rep and cap sequences are obtained from an AAV source as identified above. The AAV rep and cap sequences may be introduced into the host cell in any manner known to one in the art as described above, including, without limitation, transfection, electroporation, liposome delivery, membrane fusion techniques, high velocity DNA-coated pellets, viral infection and protoplast fusion. In one embodiment, the rep and cap sequences may be transfected into the host cell by one or more nucleic acid molecules and exist stably in the cell as an episome. In another embodiment, the rep and cap sequences are stably integrated into the genome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

The rep and cap sequences, along with their expression control sequences, may be supplied on a single vector, or each sequence may be supplied on its own vector. Preferably, the rep and cap sequences are supplied on the same vector. Alternatively, the rep and cap sequences may be supplied on a vector that contains other DNA sequences that are to be introduced into the host cells. Preferably, the promoter used in this construct may be any suitable constitutive, inducible or native promoters known to one of skill in the art. The molecule providing the rep and cap proteins may be in any form which transfers these components to the host cell. Desirably, this molecule is in the form of a plasmid, which may contain other non-viral sequences, such as those for marker genes. This molecule does not contain the AAV ITRs and generally does not contain the AAV packaging sequences. To avoid the occurrence of homologous recombination, other virus sequences, particularly those of adenovirus, are avoided in this plasmid. This plasmid is desirably constructed so that it may be stably transfected into a cell.

Although the molecule providing rep and cap may be transiently transfected into the host cell, it is preferred that the host cell be stably transformed with sequences necessary to express functional rep/cap proteins in the host cell, e.g., as an episome or by integration into the chromosome of the host cell. Depending upon the promoter controlling expression of such stably transfected host cell, the rep/cap proteins may be transiently expressed (e.g., through use of an inducible promoter).

The methods employed for constructing embodiments of this invention are conventional genetic engineering or recombinant engineering techniques such as those described in the references above. For example, the rAAV may be produced utilizing a triple transfection method using either the calcium phosphate method (Clontech) or Effectene reagent (Qiagen, Valencia, Calif.), according to manufacturer=s instructions. See, also, Herzog et al, 1999, *Nature Medic.,* 5(1):56-63, for the method used in the following examples, employing the plasmid with the transgene, CPA-RPE65, a helper plasmid containing AAV rep and cap, and a plasmid supplying adenovirus helper functions of E2A, E4Orf6 and VA. While this specification provides illustrative examples of specific constructs, using the information provided herein, one of skill in the art may select and design other suitable constructs, using a choice of spacers, promoters, and other elements, including at least one translational start and stop signal, and the optional addition of polyadenylation sites.

The rAAV virions are then produced by culturing a host cell containing a rAAV virus as described herein which contains a rAAV construct to be packaged into a rAAV virion, an AAV rep sequence and an AAV cap sequence under the control of regulatory sequences directing expression thereof. Suitable viral helper genes, e.g., adenovirus E2A, E4Orf6 and VA, among other possible helper genes, may be provided to the culture in a variety of ways known to the art, preferably on a separate plasmid. Thereafter, the recombinant AAV virion which directs expression of the transgene is isolated from the cell or cell culture in the absence of contaminating helper virus or wildtype AAV.

One may easily assay whether a particular expression control sequence is suitable for a specific transgene, and choose the expression control sequence most appropriate for expression of the desired transgene. For example, a target cell may be infected in vitro, and the number of copies of the transgene in the cell monitored by Southern blotting or quantitative polymerase chain reaction (PCR). The level of RNA expression may be monitored by Northern blotting or quantitative reverse transcriptase (RT)-PCR; and the level of protein expression may be monitored by Western blotting, immunohistochemistry, enzyme-linked immunosorbent assay (ELISA), radioimmunoassay (RIA) or by the specific methods detailed below in the examples.

In one embodiment exemplified below, a suitable recombinant vector for use in this invention is AAV-RPE65, which utilizes AAV serotype 2 ITR and capsid sequences and is described in detail in Example 1 below. This recombinant AAV contains a CMV immediate early enhancer/chicken β-actin (CβA) promoter-exon 1-intron 1 element followed by a poliovirus internal ribosome entry sequence (IRES), followed by the cDNA encoding the wildtype protein RPE65. However, the present invention is not limited to this exemplary embodiment. Similar rAAV with different transgenes, promoters, IRES, and virus capsids may be useful in this invention, as described in detail above.

D. Pharmaceutical Compositions and Methods of the Invention

The recombinant AAV containing the desired transgene and cell-specific promoter for use in the target ocular cell as detailed above is preferably assessed for contamination by conventional methods and then formulated into a pharmaceutical composition intended for subretinal injection. Such formulation involves the use of a pharmaceutically and/or physiologically acceptable vehicle or carrier, particularly one suitable for subretinal injection, such as buffered saline or other buffers, e.g., HEPES, to maintain pH at appropriate physiological levels. A variety of such known carriers are provided in International Patent Publication No. WO 00/15822, incorporated herein by reference. If the virus is to be stored long-term, it may be frozen in the presence of glycerol.

According to the method of this invention for treating an ocular disorder characterized by the defect or absence of a normal gene in the ocular cells of a human or animal subject, the pharmaceutical composition described above is administered to the subject having such a blinding disease by subretinal injection. The use of subretinal injection as the route of delivery is a critical component of this method, as intravitreal administration does not enable the same therapeutic effects. The vector and carrier cannot diffuse across the multiple cell layers in the retina to reach the RPE, when intravitreal injection is used. Similarly, intravenous delivery is unacceptable because the material does not penetrate the blood-brain (blood-retinal) barrier. Because the virus does not diffuse well, topical administration is similarly not preferred for this method. See the examples below.

An effective amount of a recombinant adeno-associated virus carrying a nucleic acid sequence encoding the desired transgene under the control of the cell-specific promoter sequence desirably ranges between about $1\times10^9$ to $2\times10^{12}$ rAAV infectious units in a volume of between about 150 to about 800 l. The rAAV infectious units are measured as described in S. K. McLaughlin et al, 1988 *J. Viral.*, 62:1963. More desirably, an effective amount is between about $1\times10^{10}$ to $2\times10^{11}$ rAAV infectious units in a volume of between about 250 to about 500 l. Still other dosages in these ranges may be selected by the attending physician, taking into account the physical state of the subject, preferably human, being treated, the age of the subject, the particular ocular disorder and the degree to which the disorder, if progressive, has developed.

It may also be desirable to administer multiple "booster" dosages of the pharmaceutical compositions of this invention. For example, depending upon the duration of the transgene within the ocular target cell, one may deliver booster dosages at 6 month intervals, or yearly following the first administration. The fact that AAV-neutralizing antibodies were not generated by administration of the rAAV vector, as discussed in the examples below, should allow additional booster administrations.

Such booster dosages and the need therefor can be monitored by the attending physicians, using, for example, the retinal and visual function tests and the visual behavior tests described in the examples below. Other similar tests may be used to determine the status of the treated subject over time. Selection of the appropriate tests may be made by the attending physician. Still alternatively, the method of this invention may also involve injection of a larger volume of virus-containing solution in a single or multiple infection to allow levels of visual function close to those found in wildtype retinas.

As is demonstrated in the examples below, an exemplary rAAVRPE65 was employed in in vitro and in vivo experiments to provide evidence of the utility and efficacy of the methods and compositions of this invention. The in vitro examples demonstrated proper expression of the transgene in an animal model of a human ocular disorder resulting in blindness. The in vivo examples demonstrated restoration of visual function and visual behavior by the method of this invention in a large animal model of a human retinopathy. The use of the exemplary vector demonstrated in both in vitro and in vivo experiments that the defect in the RPE65 mutant dog could be corrected by gene delivery. Vision was restored in this large animal model of childhood blindness. This is the first successful reversal of vision loss in a large animal model of retinal degeneration. This data allow one of skill in the art to readily anticipate that this method may be similarly used in treatment of LCA or other types of retinal disease in other subjects, including humans.

While previous studies have demonstrated that retinal degeneration can be retarded with gene therapy techniques, the present invention demonstrates a definite recovery of function. In addition, while small animal studies have demonstrated histologic and electrophysiologic correlates of visual function to be partially preserved, this large animal study has shown the presence of vision with regard to both physiological and behavioral measures.

E. Examples

As summarized, the following examples demonstrate that in three of three eyes, in vivo transfer of wildtype RPE65 to cells of the outer retina was sufficient to restore photoreceptor function in the RPE65 mutant dog. Function was not restored after intravitreal injection of vector, a route which normally results only in transduction of ganglion cells (Dudus, L., et al. *Vision Res.* 39, 2545-2554 (1999)). The virus transduced RPE cells in the immediately injected quadrant, and transduced RPE produced both wildtype RPE65 message and protein. Without being bound by theory, the inventors believe that although the rAAV virus targets photoreceptors and other retinal neurons as well as RPE cells, and the CβA promoter is active in all these cell types, it is likely that it is the expression of the wildtype transgene in RPE cells (and not photoreceptors) that rescues the mutant phenotype. The RPE alone is responsible for, and possesses the components necessary to supply chromophore for, rod photoreceptors, although the existence of a retinal retinoid metabolism for cones (not involving RPE65 gene product) remains plausible.

The following examples illustrate several embodiments of this invention. These examples are illustrative only, and do not limit the scope of the present invention.

Example 1

Virus Preparation

Recombinant AAV vector was based on pTR-UF2, a vector using the 472 by mouse rod opsin promoter to drive expression of green fluorescent protein (GFP) (Flannery, J., et al. 1997 *Proc Natl Acad Sci USA* 94, 6916-6921). To generate the recombinant vector, AAV-RPE65, the opsin promoter in pTR-UF2 was replaced with a CMV immediate early enhancer (381 bp)/chicken β-actin (CβA) promoter-exon 1-intron 1

(1352 bp) element followed by a poliovirus internal ribosome entry sequence (637 bp). The latter supports expression in photoreceptors, RPE and ganglion cells (Li and Hauswirth, unpublished data, 2000). The reporter/transgene GFP was replaced with the canine RPE65 cDNA (Aguirre, G. et al, 1998 *Mol. Vis.* 4: 23) via flanking Not I sites and the orientation and reading frame confirmed by DNA sequence analysis. Plasmid DNA containing this construct was packaged into AAV particles employing iodixanol gradient purification followed by heparin-sepharose agarose column chromatography as described in Hauswirth, W. W. et al, 2000 *Meth. Enzymol.* 316, 743-761. Vector titers were determined using an infectious center assay.

Four AAV-RPE65 virus preparations were made and combined to a total volume of 1.05 ml at $2.3 \times 10^{11}$ infectious particles/ml. Contaminating helper adenovirus and wild-type AAV, assayed by serial dilution cytopathic effect or infectious center assay, respectively were less than six orders of magnitude lower than vector AAV.

Example 2

In Vitro Testing of an AAV Carrying the Wildtype Canine RPE65 cDNA

A. RPE Cell Cultures

RPE cells from eyes of both a wildtype dog and a homozygous affected (RPE65 mutant) dog were dissociated with 0.25% trypsin (Ray, J. et al, 1997 *Curr. Eye Res.* 16: 131-143) and plated at $1-2 \times 10^5/9$ mm plastic dish. The cells were then cultured. After 48 days, confluent RPE cultures were trypsinized, subcultured and infected at 80% confluency with $2.3 \times 10^7$ AAV-RPE65 viral particles for 4 hours. Expression of the RPE65 transgene was assessed by immunohistochemistry 10 days post-infection.

B. RPE65 Immunocytochemistry and Western Analysis in Canine RPE Cells and Retina.

In order to evaluate the presence of the RPE65 protein, the cultured canine RPE cells were evaluated by immunocytochemistry by immunolabelling with a rabbit anti-RPE65 peptide polyclonal antibody (generously provided by T. M. Redmond) and the nuclei were stained with propidium iodide. For Western analysis, proteins from cultured RPE were electrophoresed on 12.5% SDS-polyacrylamide gel and then electrotransferred on nitrocellulose membrane Immunodetection was performed using the anti-RPE65 antibody followed by goat anti-rabbit secondary antibody and $^{125}$I-protein A (Verdugo, M., et al. 1998 *Invest Ophthalmol Vis Sci* 39, S719).

In the resulting immunohistochemical sections (not shown) wildtype retinal cells labeled uniformly and intensely with the anti-RPE65 antibody, i.e., they possessed high levels of RPE65. In contrast, RPE65 labeling (i.e., RPE protein) was absent in untreated RPE65 mutant cells, 60 days in culture, prior to infection with AAV-RPE65, showing only background autofluorescence. Further, lipid inclusions were apparent in the diseased RPE cells. However, within 10 days of infection of the RPE65 mutant cells (60 days in culture) with AAV-RPE65, the majority of cells labeled positively with the anti-RPE65 antibody, indicating presence of wildtype RPE65 protein. One cell did not appear to have been transduced. Complementary results were observed following immunohistochemistry of sections from untreated wildtype versus mutant RPE65+canine retinas.

Infection of the defective RPE cells by AAV-RPE65 and subsequent expression of the wildtype RPE65 transgene were further confirmed in vitro using PCR amplification and Western analysis, respectively.

PCR studies took advantage of the difference in size of the wildtype versus mutant canine RPE65 transcripts due to the 4 bp deletion in the latter. PCR amplification utilized RPE65-1 (forward) and RPE65-3 (reverse) primers flanking the RPE65 mutant deletion site (Aguirre, G. et al, 1998 *Mol. Vis.* 4:23). PCR conditions were 94° C. (30 seconds), 60° C. (30 seconds), and 72° C. (1 minute) for 34 cycles. PCR products were separated on a 6% polyacrylamide gel. AAV-RPE65 was used as positive control. This protocol was also used for PCR screening for shedding virus.

The PCR primers flanking this region amplified the wildtype 109 by RPE65 DNA fragment in transduced RPE cells from an affected dog. Non-transduced RPE from the same animal yielded only mutant DNA (105 bp) and normal RPE yielded only the wildtype allele (109 bp). Expression of wildtype RPE65 in transduced RPE cells from an affected animal was also apparent by Western blot analysis of cell lysates. RPE65 expression was detected only in the transduced RPE cells; not in uninfected cells.

Example 3

In Vivo Studies in the RPE65 Mutant Dog

A. Ocular Delivery

Effects of intraocular delivery of AAV-RPE65 were studied in four RPE65 mutant dogs. For in vivo studies, virus was delivered subretinally or intravitreally under direct surgical visualization using methods described previously (Bennett, J., et al. 1999 *Proc. Natl. Acad. Sci. USA* 96, 9920-9925 and Bennett, J. et al, 2000 *Meth. Enzymol.* 316, 777-789). Five eyes from three dogs (BR29, BR33 and BR47) were injected either subretinally or intravitreally with AAV-RPE65; the sixth eye was untreated (Table 1). The fourth dog (BR46) was maintained as an untreated control.

Each 150-200 µl subretinal injection of vector (at a concentration of $2.3 \times 10^{11}$ infectious particles/ml) created a retinal detachment elevating approximately 35% of the total retinal area. In 2 eyes (BR33 and BR47) this detachment primarily occupied the nasal-inferior quadrant; in the 3rd eye (BR29) the site was temporal-superior. These detachments resolved spontaneously within 24 hours. Animals were evaluated post-operatively for evidence of ocular or systemic toxicity, virus exposure to extralocular tissue, virus shedding, unfavorable immune response or other untoward effects. As discussed in detail below, none was found.

B. Detection of Inflammation

Eyes were evaluated clinically at regular intervals following the surgery to identify inflammation. Humoral and intraocular antibodies specific to AAV capsid proteins were evaluated as described in Bennett, J., et al. 1999 *Proc. Natl. Acad. Sci. USA* 96, 9920-9925, incorporated herein by reference. Post-operatively, there was no evidence of ocular or systemic toxicity, or other untoward effect. Hematology and blood chemistries revealed no evidence of systemic toxicity. Evaluation of humoral response prior to and post treatment revealed slightly elevated anti-AAV capsid titers in pre-treatment serum samples, suggesting previous exposure to AAV proteins. Antibody titers were increased in two of the three dogs one month after exposure and in all three dogs 4 months after exposure. Non-neutralizing serum antibodies directed against RPE65 protein also increased after intraocular exposure to AAV-RPE65.

C. Transgene Expression and Persistence

To correlate transgene expression with changed visual function, one subretinally injected eye (BR29, right eye) was surgically enucleated 99 days post injection. The eyecup was divided into temporal-superior, temporal-inferior, nasal-superior, and nasal-inferior quadrants. From each quadrant, the retina, and the pooled RPE-plus-choroid tissues, were separately harvested and dissected under RNase free conditions and rapidly frozen. Total RNA was prepared from retina and RPE/choroid using the TRIzol Reagent kit (Life Technologies, Gaithersburg, Md.). DNA was extracted from the same tissues according to the vendor's protocol. cDNA was amplified from total RNA using RNA PCR kit (Perkin Elmer, Foster City, Calif.) and the conditions listed above.

RPE65 expression in neural retina, RPE/choroid, and cultured RPE cells were detected. Genomic PCR demonstrates persistence of transferred viral DNA in neural retina and RPE-choroid from the injected temporal-superior quadrant. In other quadrants, the host DNA amplified preferentially and the viral DNA amplification product is below detectable levels. From noninfected RPE of the affected dog, only mutant product amplifies, but 10 days posttransfection in vitro the normal transgene yields the overwhelming product.

RT-PCR (figures not shown) demonstrated expression of wildtype message in neural retina from all 4 quadrants, but in RPE-choroid from the injected quadrant only. Where both products amplify, additional bands representing heteroduplexes are also seen. The transfected RPE/choroid from the injected quadrant expressed higher levels of the transferred cDNA than of the mutant host gene. This was not so in other quadrants. Although transfection of neural retina led to expression of the wildtype allele in all quadrants, a gradient was present in the relative intensities of the two alleles among quadrants. In the injected quadrant, the wildtype allele yielded a much more intense band than the host mutant allele. From the quadrant below this, the two bands were approximately equal in intensity. In the nasal half of the eye, the mutant band predominated.

Western analysis demonstrated absence of RPE65 protein in mutant RPE cells prior to transfection, but presence of the protein afterwards. Proteins were labeled with anti-RPE65 antibody.

By PCR analyses of serum and tear fluid, there was no sign of virus shedding at 1 month after injection (data not shown). Reverse transcriptase (RT)-PCR on sera, conjunctiva, eyelids, the gland of the third eyelid, and the optic nerve from the enucleated eye of BR29 were negative for the transgene at 103 days post injection, indicating that virus escape to extraocular tissues was below detectable levels.

D. Retinal/Visual Function Testing

1. Electroretinograms (ERGS)

The physiological consequences of the treatments were assessed by electroretinography (ERG) (Banin, E., et al. 1999 Neuron 23, 549-57). Dogs were dark-adapted (overnight), premedicated with acepromazine (0.55 mg/kg, IM) and atropine (0.03 mg/kg, IM) and anesthetized by intermittent ketamine (15 mg/kg, IV, repeated every 15 minutes). Pulse rate, oxygen saturation and temperature were monitored throughout. The cornea was anesthetized with topical proparacaine HCl (1%) and pupils dilated with cyclopentolate (1%) and phenylephrine (2.5%).

Full field ERGs were recorded using a computer-based system (EPIC-XL, LKC Technologies, Inc., Gaithersburg, Md.) and Burian-Allen contact lens electrodes (Hansen Ophthalmics, Iowa city, Iowa) (Banin, E., et al. 1999 Neuron 23, 549-57). Dark-adapted luminance-response functions were obtained with blue (Wratten 47A) flash stimuli spanning ~6 log units (−2.9 to +2.8 log scot-cd.s.m$^{-2}$).

ERG b-wave amplitudes were measured conventionally from baseline or a-wave trough to positive peak; a-wave amplitude was measured from baseline to negative peak at the maximal stimulus. For isolating cone pathway function, dogs were light-adapted and 29 Hz flicker ERGs evoked with white flash stimuli (0.4 log cd.s.m$^{-2}$) on a background (0.8 log cd.m$^{-2}$); amplitudes were measured between successive negative and positive peaks and timing from stimulus to the next positive peak. Ocular axial length and pupil diameter were measured for each experiment to permit calculation of retinal illuminance.

The restoration of retinal/visual function in RPE65 mutant dogs by subretinal AAV-RPE65 was demonstrated by the results of the above-described ERGs. A comparison of dark-adapted ERGs evoked by increasing intensities of blue light stimuli in a control dog with ERGs to the same stimuli in RPE65 mutant dog BR33 showed the affected animal had elevated thresholds, reduced amplitudes and waveform shape changes (i.e., b-waves but no detectable a-waves). Over a 5 log unit range of increasing stimulus intensity, the ERG of normal dogs responded with increasing amplitude of bipolar cell (b-wave) and photoreceptor (a-wave) components. At all intensities these signals were dominated by rod photoreceptor retinal pathways. Compared to normal dogs, the threshold stimulus required to elicit an ERG response from 4 month old RPE65 mutant dogs was elevated by over 4.5 log units.

Retinal function was dramatically improved in eyes treated with subretinal AAV-RPE65, compared to pre-treatment recordings. After subretinal AAV-RPE65 therapy, the mutant dog showed a vastly improved b-wave threshold, a large increase of a- and b-wave amplitudes (although not to normal levels) and an ERG waveform shape that is similar to controls. Responses from the right eye of BR33 had b-wave thresholds lower by ~4 log units than pre-treatment, and appeared similar to normal.

The details of photoreceptor function were analyzed by the amplitude and timing of the ERG photoresponses evoked by 2.8 log scot-cd.s.m$^{-2}$ flashes. Recordings from three control dogs showed ~250 μV saturated amplitudes peaking between 4.5 to 6 ms. Photoreceptor function was near noise level in three untreated eyes of RPE65 mutant dogs and two eyes treated with intravitreal AAV-RPE65. Photoresponses (of reduced amplitude but normal timing) were present in all three eyes that received subretinal AAV-RPE65. ERG photoresponses in the three subretinally injected eyes showed maximal amplitudes of 27, 36 and 58 μV, representing ~16% of normal (mean±SD=246±95 μV; n=7).

Small responses evoked at higher intensities lacked an a-wave. Higher energy stimuli and recording criteria that elicit, in normal dogs, saturated ERG photoresponses originating from photoreceptors yielded no detectable signals in affected animals. A flicker ERG response, representing isolated cone pathway function in normals, was absent in affected animals. Photoresponse amplitudes in subretinally injected eyes were significantly different (P<0.05) than the amplitudes in untreated eyes (14±3.4 μV; n=3).

Flicker ERGs in the same eyes as described in the immediately preceding paragraphs demonstrated a lack of detectable cone-mediated responses from RPE65 mutant dogs with untreated or intravitreally treated eyes. All eyes with subretinal AAV-RPE65 treatment recovered cone flicker responses. Cone flicker ERGs were readily recordable post-treatment; amplitudes ranged from 4 to 6 μV, representing ~16% of normal (30±8 µV). Intravitreally injected eyes showed no difference from untreated eyes for all measured ERG parameters.

2. Pupillometry

Transmission of retinal activity to higher visual pathways was demonstrated by pupillometry. Dogs were dark-adapted for more than 3 hours and pupil responses were obtained sequentially from each eye using full-field green stimuli (−3.2 to +3.0 log scot-cd.m$^{-2}$) of ~2 second duration. Pupils were imaged with a video camera under infrared illumination and continuously recorded on a VCR. Dynamic changes in pupil diameters were measured from single frames displayed on the video monitor in relation to the timing of each stimulus. Pupil responses were calculated by subtracting the smallest pupil diameter achieved within 2 seconds after the stimulus onset from the diameter measured in the dark.

All tested pupils constricted in response to high intensity stimuli. Pupil response as a function of stimulus intensity showed 3.8 log unit elevation of threshold (1 mm response criterion) in untreated eyes (n=3; two eyes of BR46 and one eye of BR29) compared to normal eyes (n=3). Eyes treated with subretinal AAV (n=2; BR33 and BR47) had 0.8 log unit lower thresholds compared to untreated eyes.

A change in pupil diameter was noted in response to 2.5 log cd.m$^{-2}$ green stimulus in one eye of three representative dogs; untreated (BR46), subretinal AAV treated (BR33) and a normal control.

At a suprathreshold intensity, pupillary constriction was greatest in normal dogs and least in untreated RPE65 mutant dogs. Subretinally-treated eye of BR33 responded midway between normal and untreated. The threshold intensity to reach a criterion pupillary response was improved in subretinally-treated eyes compared with untreated eyes.

Consistent with ERG and pupillometry results, at 104 days post-treatment, flash evoked visual cortical potentials to a series of increasing intensities of blue light (Wratten 47) in the dark-adapted state and recorded definite waveforms from the subretinally-treated eye. In contrast there were no consistent waveforms at any intensity from the eye treated intravitreally.

3. Behavioral Testing

Qualitative visual assessment of the 3 treated animals was performed at 4 months post injection using an obstacle course and observers masked to the experimental design. Visual behavior was also documented by video recording. Results of behavioral testing were consistent with the electrophysiological results.

For example, dog BR33 was consistently (5/5 observers) scored as "normally sighted" under photopic (room lighting) conditions. Under dim red light this dog consistently avoided objects either directly in front of her, or to her right (the side injected subretinally), but consistently failed to avoid objects on the left (injected intravitreally). In contrast, the untreated control affected dog, BR46 walked into objects ahead of her and at either side.

Table 1 provides the data collected from the procedures performed on the eyes of four RPE65 mutant dogs. In the Table, age is recorded as days postnatal. The abbreviation Rt is used for right eye, while left is indicated for left eye. The routes of injection are identified as SR for subretinal injection, IV for intravitreal injection, and NI for not injected. The doses are reported as No.×10$^{10}$ infectious particles of recombinant AAV-RPE65 virus injected. Baseline ERGs were recorded 2 weeks prior to injection. Rescue Effect was assessed by ERGs recorded 95 days after injection. Positive effect is indicated by POS. NEG indicates no effect apparent.

TABLE 1

| Animal | Age at Day 0 | Eye | Route of Injec = n | Dose | Volume (µL) | Age at ERG | ERG Rescue Effect |
|---|---|---|---|---|---|---|---|
| BR29 | 132 | Rt | SR | 3.7 | 150 | 227 | POS |
|  |  | Left | NI | — | — | 227 | NEG |
| BR33 | 124 | Rt | SR | 4.6 | 200 | 219 | POS |
|  |  | Left | IV | 4.6 | 200 | 219 | NEG |
| BR47 | 108 | Rt | SR | 4.6 | 200 | 203 | POS |
|  |  | Left | IV | 4.6 | 200 | 203 | NEG |
| BR46 | 108 | Rt | NI | — | — | 203 | NEG |
|  |  | Left | NI | — | — | 203 | NEG |

All references and documents disclosed above are incorporated by reference herein. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for treating a human subject having Leber Congenital Amaurosis, the method comprising:
   administering to the subject by subretinal injection a recombinant adeno-associated virus (rAAV) comprising a nucleic acid sequence encoding a normal retinal pigment specific epithelial 65 (RPE65) gene operably linked to a chicken beta actin promoter/CMV enhancer, wherein said rAAV is administered in a dosage of from $1 \times 10^9$ to $2 \times 10^{12}$ rAAV in a volume comprising about 150 microliters, thereby restoring visual function in said subject.

2. The method according to claim 1, wherein said rAAV is administered in a volume comprising about 250 microliters.

3. The method according to claim 1, wherein said rAAV is administered in a volume of between 150 to 800 microliters.

4. The method according to claim 1, wherein said rAAV is administered in a volume comprising of between 250 to 500 microliters.

5. The method according to claim 1, wherein said rAAV is administered in a volume comprising about 500 microliters.

6. The method according to claim 1, wherein said rAAV is administered in a volume comprising about 800 microliters.

7. The method according to claim 1, wherein said rAAV is administered in a dosage of from $1 \times 10^{10}$ to $2 \times 10^{11}$ rAAV in a volume of between 250 to 500 microliters.

8. The method according to claim 1, wherein said ocular cells are retinal pigment epithelial cells.

* * * * *